United States Patent [19]
Bang et al.

[11] Patent Number: 5,571,804
[45] Date of Patent: Nov. 5, 1996

[54] CEPHALOSPORIN ANTIBIOTICS

[75] Inventors: Chan S. Bang; Jae H. Yeo; Young M. Woo; Jong C. Lim; Deog H. Yang, all of Daejeon; Se H. Kim, Seoul; Jae H. Jeon, Seoul; Mi K. Seo, Seoul; Sam S. Kim, Daejeon; Tae H. Lee, Daejeon; Yong Z. Kim, Daejeon; Hun S. Oh, Daejeon, all of Rep. of Korea

[73] Assignee: Lucky Limited, Seoul, Rep. of Korea

[21] Appl. No.: 303,930

[22] Filed: Sep. 9, 1994

[30] Foreign Application Priority Data

Sep. 11, 1993 [KR] Rep. of Korea ............... 93-18319

[51] Int. Cl.$^6$ ............... C07D 501/60; A61K 31/545
[52] U.S. Cl. ............... 514/203; 514/204; 514/205; 514/206; 540/225; 540/227
[58] Field of Search ............... 540/227, 225; 514/206, 203, 204

[56] References Cited

U.S. PATENT DOCUMENTS

| | | | |
|---|---|---|---|
| 5,001,121 | 3/1991 | Ohnishi et al. | 514/206 |
| 5,234,920 | 8/1993 | Okita et al. | 514/202 |
| 5,292,733 | 3/1994 | Kim et al. | 540/227 |

FOREIGN PATENT DOCUMENTS

| | | |
|---|---|---|
| 0272487A1 | 6/1988 | European Pat. Off. . |
| 0397511A2 | 11/1990 | European Pat. Off. . |
| 0508375A2 | 10/1992 | European Pat. Off. . |
| 0520880A1 | 12/1992 | European Pat. Off. . |
| WO92/03445 | 3/1992 | WIPO . |

*Primary Examiner*—John M. Ford
*Attorney, Agent, or Firm*—Anderson Kill & Olick, P.C.

[57] ABSTRACT

Cephalosporin compounds of formula (I):

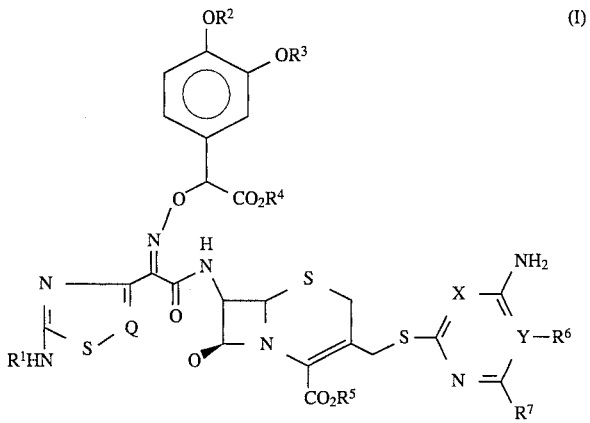

wherein:
$R^1$ is a hydrogen or an amino protecting group;
$R^2$ and $R^3$ are, independently, a hydrogen or a hydroxy protecting group, or form together a cyclic diol protecting group;
$R^4$ and $R^5$ are, independently, a hydrogen or a carboxyl protecting group;
X and Y are a nitrogen and a carbon atom, respectively, or a carbon and a nitrogen atom, respectively;
$R^6$ and $R^7$ are, independently, a hydrogen or an amino, substituted amino, hydroxy, alkoxy, $C_{1-4}$ alkyl, carboxyl or alkoxy carbonyl group, or jointly form a $C_{3-7}$ cycloalkyl group together with the carbon to which they are attached, when X and Y are a nitrogen and a carbon, respectively, or $R^7$ is a hydrogen or an amino group when X and Y are a carbon and a nitrogen, respectively; and
Q is =CH— or =N—, or pharmaceutically acceptable non-toxic salts, physiologically hydrolyzable esters, hydrates and solvates and isomers thereof, and isomers thereof possess potent and broad antibacterial activities.

5 Claims, No Drawings

CEPHALOSPORIN ANTIBIOTICS

FIELD OF THE INVENTION

The present invention relates to novel cephalosporin compounds and pharmacologically acceptable non-toxic salts, physiologically hydrolyzable esters, hydrates and solvates, and isomers thereof, which possess potent and a broad spectrum of antibacterial activities. The invention also relates to processes for preparing these compounds and to pharmaceutical compositions containing same as active ingredients.

BACKGROUND OF THE INVENTION

Antibiotics of cephalosporin series are widely used for the treatment of diseases which are caused by general pathogenic bacteria in human beings and animals. Particularly, such antibiotics have been found to be useful for the treatment of diseases caused by bacteria exhibiting resistance to other antibiotics, e.g., penicillin-resistant bacteria; and also for the treatment of penicillin-hypersensitive patients.

In most circumstances, it is desirable to employ antibiotics possessed with broad antibacterial activities, e.g., against both Gram-positive and Gram-negative bacteria. It is well known that the activity of a cephalosporin compound generally depends upon the substituent on the 3- or 7-position of the cephem ring. In this regard, there have been many studies made in developing a variety of cephalosporin antibiotics with such broad spectrum of antibiotic activities by introducing a 7-β acylamido group and various substituents on the 3-position of the cephem ring.

For example, GB Patent No. 1,399,086 discloses cephalosporin derivatives of formula (A):

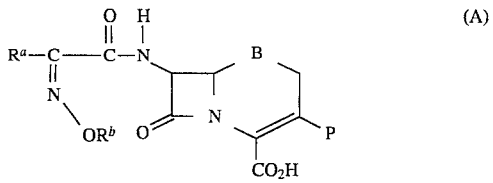

wherein:
$R^a$ represents a hydrogen or an organic group;
$R^b$ represents an etherified mono-valent organic group;
B represents S or S→O; and
P represents an organic group.

Stimulated by the discovery of these compounds, there have followed numerous antibiotic compounds having improved efficacy properties with respect to certain microorganisms, especially against Gram-negative bacteria, including those compounds disclosed in GB Patent No. 1,522,140 which have the following formula (B) and exist as a syn isomer or as a mixture of syn and anti isomers wherein the syn isomer is present in an amount of at least 90%:

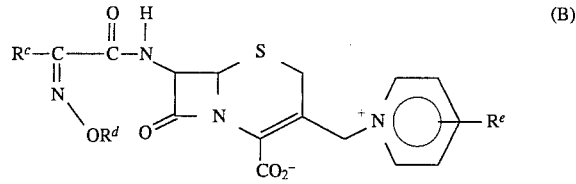

wherein:
$R^c$ represents a furyl or thienyl group;
$R^d$ represents a $C_{1-4}$ alkyl, $C_{3-4}$ cycloalkyl, furylmethyl or thienylmethyl group; and
$R^e$ represents a hydrogen, or a carbamoyl, carboxymethyl, sulfonyl or methyl group.

Thereafter, further efforts have been made to prepare new and improved cephalosporin compounds having antibiotic properties against both Gram-positive and Gram-negative bacteria and, as a result, cephalosporin compounds having a modified but similar structure to the formula (A) or (B) have been developed.

For example, Belgian Patent No. 852,427 discloses a cephalosporin antibiotic of formula (A) in which $R^a$ is substituted with various organic groups including 2-aminothiazol-4-yl and the oxygen of oxyamino group is attached to an aliphatic carbon which itself can be substituted with a carboxyl group, and the substituent on the C-3 position is an acyloxymethyl, hydroxymethyl, formyl or optionally substituted heterocyclic thiomethyl group.

Compounds having strong antibiotic activities against some of the Gram-negative bacteria producing β-lactamase in addition to other pathogenic bacteria have been studied to develop certain cephalosporin compounds with α-carboxy-3,4-substituted benzyl group as the $R^b$ group has been known to show a strong activity against a wide range of pathogenic bacteria.

PCT/JP86/00140 discloses cephem compounds of formula (C):

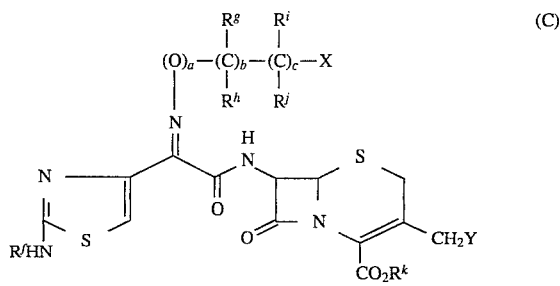

wherein:
$R^f$ represents a hydrogen or an amino protecting group;
$R^g$ and $R^h$ represent a hydrogen or oxygen, or a methyl, carboxyl or protected carboxyl group, respectively;
$R^i$ and $R^j$ represent a hydrogen or oxygen, respectively;
$R^k$ represents a hydrogen or a carboxyl protecting group;
a, b and c are 0 or 1, independently;
X is a hydrogen, a hydroxyl group or

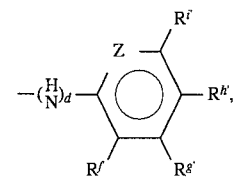

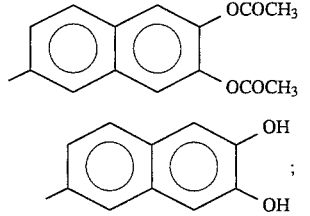

Y represents a carbon or nitrogen; and
Z represents a halogen, an acetoxy or heterocyclic group.

European Patent Appl. No. 87308525.2 gives a cephem compound of formula (D):

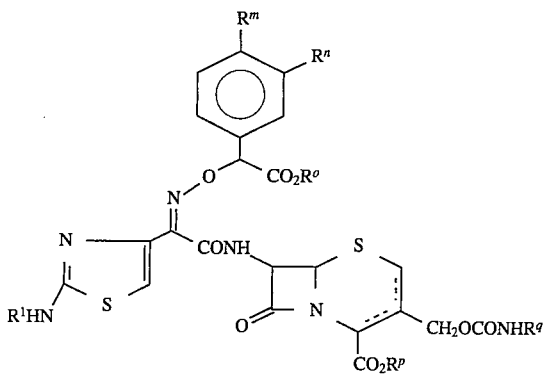

wherein:

$R^l$ represents a hydrogen or an amino protecting group;

$R^m$ and $R^n$ represent a hydroxy or substituted hydroxy group independently, or they can link together to form a protected diol;

$R^o$ and $R^p$ represent a hydrogen or a carboxyl protecting group, independently;

$R^q$ represents a hydrogen or a $C_{1-4}$ alkyl group substituted with 1 to 3 halogens; and the dotted line represents a 2-cephem or 3-cephem compound.

German Patent Application No. 2714880.7 discloses cephalosporin compounds of formula (E):

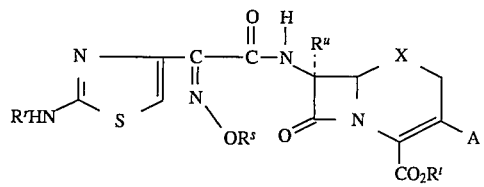

wherein:

$R^r$ represents a hydrogen, or a substituted or unsubstituted alkyl, acyl, arylsulfonyl, alkylsulfonyl or amino protecting group;

$R^s$ represents a hydrogen, or a substituted or unsubstituted alkyl, alkenyl, alkynyl, cycloalkyl, aralkyl, acyl, aryl, alkylsulfonyl, arylsulfonyl or heterocyclic group;

$R^t$ represents a hydrogen, an ester group or anion;

$R^u$ represents a hydrogen or a lower alkyloxy group;

X represents S, O, $CH_2$ or NH; and

A represents a hydrogen or halogen, or a substituted or unsubstituted alkenyloxy or —$CH_2Y$ wherein Y represents a hydrogen or halogen or a moiety of a cyclic compound.

SUMMARY OF THE INVENTION

Unexpectedly, it has been found that cephem compounds having an optionally substituted 4- and/or 6-aminopyrimidinylthiomethyl group on the C-3 position and (Z)-2-(2-aminothiazol-4-yl)-2-(α-carboxyl-3,4-disubstituted benzyloxyimino)acetamide on the 7-β position show superior antibiotic activities against various pathogenic bacteria.

Accordingly, it is a primary object of the present invention to provide the novel cephalosporin compounds and their pharmacologically acceptable non-toxic salts, physiologically hydrolyzable esters, hydrates and solvates, and isomers thereof.

It is another object of the present invention to provide processes for preparing such compounds.

It is a further object of the present invention to provide pharmaceutical compositions containing same.

In accordance with one aspect of the present invention, there are provided novel cephalosporin compounds of formula (I):

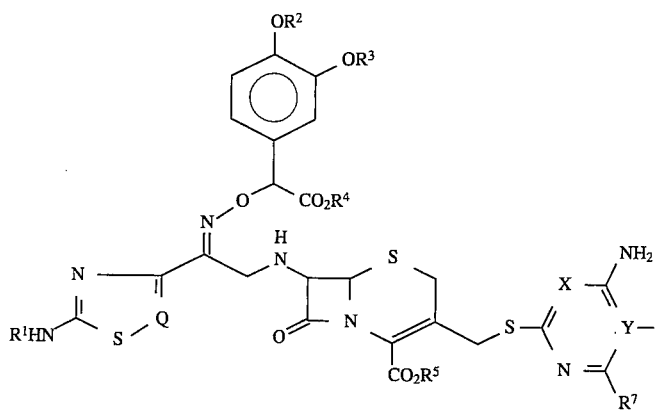

wherein:

$R^1$ is a hydrogen or an amino protecting group;

$R^2$ and $R^3$ are, independently, a hydrogen or a hydroxy protecting group, or form together a cyclic diol protecting group;

$R^4$ and $R^5$ are, independently, a hydrogen or a carboxyl protecting group;

X and Y are a nitrogen and a carbon atom, respectively, or a carbon and a nitrogen atom, respectively;

$R^6$ and $R^7$ are, independently, a hydrogen or an amino, substituted amino, hydroxy, alkoxy, $C_{1-4}$ alkyl, carboxyl or alkoxy carbonyl group, or jointly form a $C_{3-7}$ cycloalkyl group together with the carbon to which they are attached, when X and Y are a nitrogen and a carbon, respectively, or $R^7$ is a hydrogen or an amino group when X and Y are a carbon and a nitrogen, respectively; and Q is =CH— or =N—.

In accordance with another aspect of the present invention, there are provided processes for preparing the cephalosporin compounds of formula (I).

In accordance with a further aspect of the present invention, there are provided pharmacologically acceptable non-toxic salts, physiologically hydrolyzable esters, hydrates and solvates of the compounds of formula (I).

In accordance with still another aspect of the present invention, there are provided pharmacological compositions comprising one or more of the cephalosporin compounds represented by formula (I) and their afore-mentioned derivatives as an active ingredient and their pharmaceutically acceptable carriers.

DETAILED DESCRIPTION OF THE INVENTION

The novel cephalosporin compounds of formula (I) include both syn isomers and mixtures of syn and anti isomers, which mixtures contain at least 90% of the syn isomer, as well as their derivatives mentioned above. In formula (I), the carbon to which 3,4-substituted phenyl is attached is an asymmetric center to form diastereomers which are also included within the scope of the present invention, as well as mixtures thereof.

In addition, the compounds of formula (I) in accordance with the present invention may exist in tautomeric forms and such tautomers are also included within the scope of the invention. Namely, when Q is CH, the aminothiazolyl group undergoes tautomerism to form an iminotiazolinyl group to yield its tautomers which may be represented as:

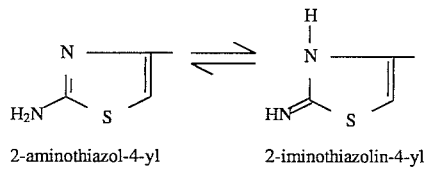

2-aminothiazol-4-yl      2-iminothiazolin-4-yl

When Q is N, the aminothiadiazol group forms tautomers with the iminothiadiazoline group which are also included in the present invention, as follows:

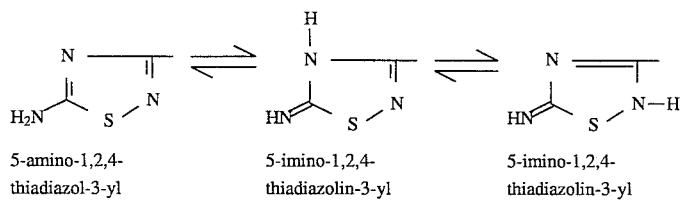

5-amino-1,2,4-thiadiazol-3-yl      5-imino-1,2,4-thiadiazolin-3-yl      5-imino-1,2,4-thiadiazolin-3-yl Among the compounds of the present invention, preferred are those wherein: all of $R^1$, $R^4$ and $R^5$ are a hydrogen; $R^2$ and $R^3$ are independently a hydrogen or an acetyl group; $R^6$ is a hydrogen or a methyl group and $R^7$ is a hydrogen or an amino group, or they form a cyclopentane or cyclohexane ring when X and Y are a nitrogen and a carbon atom, respectively, or $R^7$ is a hydrogen or an amino group when X and Y are a carbon and a nitrogen atom, respectively.

Suitable pharmacologically acceptable salts of the cephalosporin compounds (I) are conventional non-toxic salts and may include: inorganic acid salts (e.g., hydrochloride, hydrobromide, sulfate, phosphate, et.); organic carboxylic and sulfonic acid salts (e.g., formate, trifluoroacetate, citrate, acetate, maleate, tartrate, oxalate, succinate, benzoate, fumarate, mandelate, ascorbate, malate, methanesulfonate, paratoluenesulfonate, etc.); and inorganic and organic base salts such as salts with alkali metal hydroxides (e.g., sodium hydroxide, potassium hydroxide, etc.), alkaline earth metal or alkali metal carbonates (e.g., sodium bicarbonate, potassium bicarbonate, sodium carbonate, potassium carbonate and calcium carbonate, etc.) and amino acid salts.

The physiologically hydrolyzable esters of the compounds(I) may include, for example, indanyl, phthalidyl, methoxymethyl, pivaloyloxymethyl, glycyloxymethyl, phenylglycyloxymethyl and-5-methyl-2-oxo-1,3-dioxolan-4-yl-methyl ester, and other physiologically hydrolyzable esters which have been widely used in the penicillin and cephalosporin antibiotic art. These salts and esters can be prepared in accordance with known methods in the art.

A compound of formula (I) may be prepared by reacting a compound of formula (II) with a compound of formula (III) in the presence of a solvent, and, if necessary, removing the amino or carboxylic acid protecting group or reducing $S \rightarrow (O)_m$:

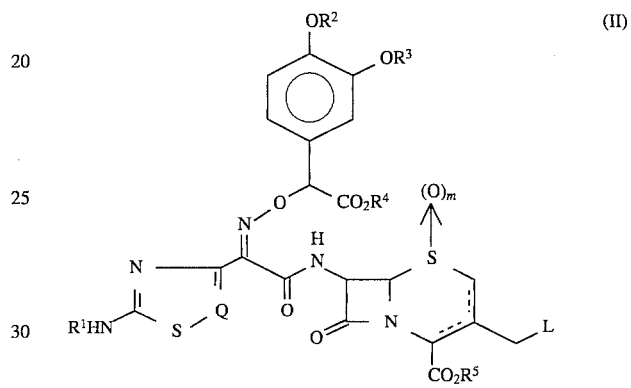

wherein:
$R^1$ to $R^7$ X Y and Q have the same meanings as defined above;
L is a leaving group; and
m is 0 or 1.

The amino protecting group in $R^1$ above may be those groups which can be readily removed under the conventionally need mild conditions to form a free amino group and may include: acyl, substituted and unsubstituted aryl(lower)alkyl(e.g., benzyl, diphenylmethyl and triphenylmethyl), (lower) alkoxyaryl (e.g., 4-methoxybenzyl), halo(lower)alkyl(e.g., trichloromethyl and trichloroethyl), tetrahydropyranyl, substituted phenylthio, substituted alkylidene, substituted aralkylidene and substituted cycloalkylidene. The acyl group as an amino protecting group may include, for example, $C_{1-5}$ alkanoyl (e.g., formyl and acetyl), and aryl (lower) alkoxycarbonyl (e.g., benzyloxycarbonyl), where the acyl group can be substituted with 1 to 3-substituents such as a halogen, a hydroxy, cyano and nitro group. In addition, the amino protecting group may include the reaction products obtained from reacting amino groups with silane, boron or phosphorous compounds.

The hydroxy protecting group in $R^2$ or $R^3$ may include, for example, acyl [e.g., formyl or —$COR^a$, wherein $R^a$ is a $C_{1-8}$alkyl(e.g., acetyl)], alkoxycarbonyl [e.g., —$CO_2R^a$ wherein $R^a$ is a $C_{1-8}$ alkyl], silyl [e.g., ($C_{1-4}$ alkyl)silyl(e.g., trimethylsilyl and t-butyldimethylsilyl)], borate and phosphate [—B ($OR^b$) or —P(O)($OR_b$)2, wherein $R^b$ is a $C_{1-4}$ alkyl]; and cyclic diol protecting group formed by both $R^2$ and $R^3$ may include, for example, a $C_{1-7}$ alkylidenedioxy(e.g., methylenedioxy, ethylenedioxy or isopropylidenedioxy), a substituted alkylidenedioxy(e.g., methoxymethylenedioxy, diphenylmethylenedioxy or carbonyldioxy), cyclic borate (e.g., —OB(OH)O—), cyclic phosphate (e.g., —OP(O)(OH)O— or —OP(O)($OR^b$)O—wherein $R^b$ is a $C_{1-4}$ alkyl) and di ($C_{1-4}$ alkyl)silyldioxy (e.g., dimethylalkyldioxy).

The carboxyl protecting group in $R^4$ or $R^5$ may be any one of those which can be readily removed under the conventional mild conditions to form a free carboxyl group and may include, for example, (lower)alkylesters (e.g., methyl ester and tertbutyl ester), (lower)alkenylesters (e.g., vinylester and allylester), (lower)alkoxy(lower)alkylesters (e.g., methoxymethylester), halo (lower) alkylesters (e.g., 2,2,2-trichloroethylester), substituted and unsubstituted aralkyl esters (e.g., benzylester and p-nitrobenzyl ester), (lower) aralkoxy esters (e.g., p-methoxybenzyl ester) and silyl esters.

The amino, hydroxy, cyclic diol or carboxyl protecting group can be properly selected after considering the chemical property of the desired compound(I).

The leaving group L in formula (II) may include, for example, a halogen such as chlorine, fluorine and iodine, a (lower) alkanoyloxy group such as acetoxy, a (lower)alkanesulfonyloxy group such as methanesulfonyloxy, an arenesulfonyloxy group such as p-toluenesulfonyloxy, an alkoxycarbonyloxy group and the like.

The term "lower" as used hereinabove and elsewhere in this specification, for example, in reference to "lower alkyl", encompasses those compounds having 1 to 6 carbon atoms, more preferably, 1 to 4 carbon atoms.

The dotted line of formula(II) which are starting materials for the of preparation cephalosporin compounds represents a single or double bond; and, therefore, the compounds of formula(II) may be the compounds of formula(II-a), or the compounds of formula(II-b), or mixtures thereof:

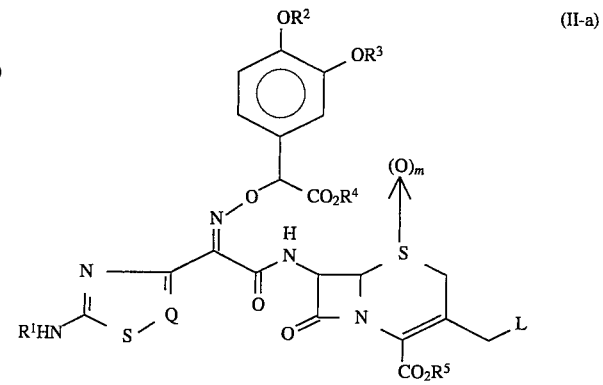

(II-a)

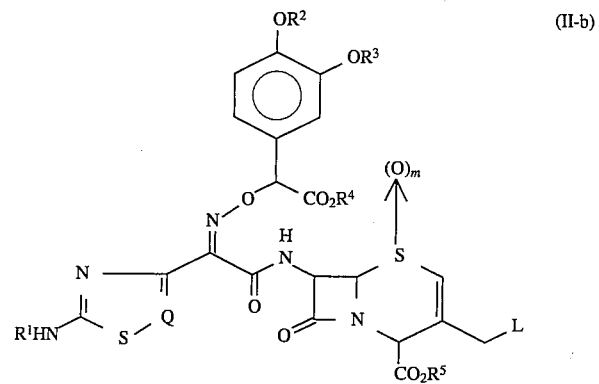

(II-b)

wherein $R^1$ to $R^5$, Q, m and L have the same meanings as defined before.

The compounds of formula(II) may be prepared by activating a compound of formula(IV) or, salts thereof with an acylating agent and then reacting with a compound of formula(V) in accordance with the following scheme(A).

Scheme A

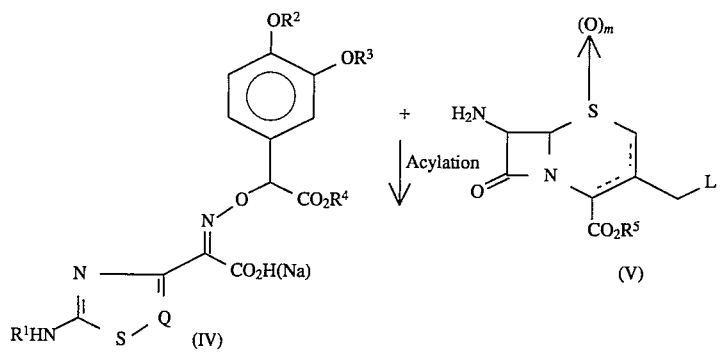

-continued
Scheme A

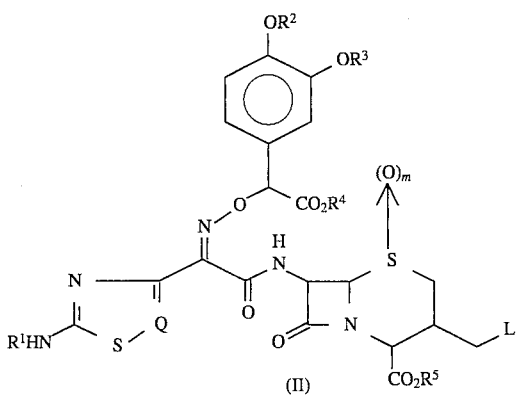

(II)

wherein:
$R^1$ to $R^5$, m and L have the same meanings as defined previously. The dotted line of formula(V) represents a single or double bond; and therefore, the compounds of formula(V) may be the compounds of formula(V-a) or the compounds of formula(V-b), or mixtures thereof:

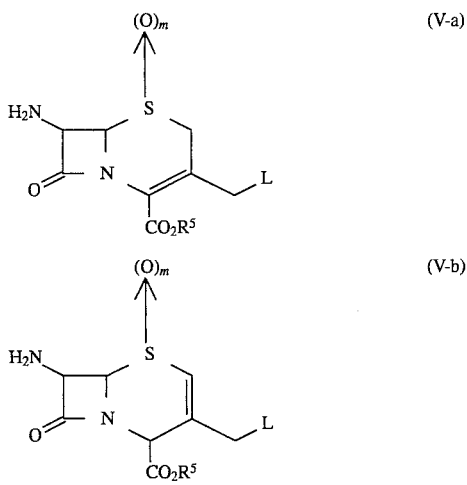

wherein:
$R^5$, m and L have the same meanings as defined previously.

The acylated derivative from the compound of formula(IV) may be an acid chloride, anhydrous acid, mixed anhydrous acid (preferably, anhydrous acid formed with methyl chloroformate, mesitylenesulfonyl chloride, p-toluenesulfonyl chloride or chlorophosphate) or activated ester (preferably an ester formed by reaction with N-hydroxy benzotriazole in the presence of a condensing agent, e.g., dicyclohexyl carbodiimide). The acylation may be conducted by using a free acid of the compound(IV) in the presence of a condensing agent, e.g., dicyclohexyl carbodiimide or carbonyl diimidazole. Further, the acylation may be conventionally conducted in the presence of an organic base, e.g., a tertiary amine(preferably, triethyl amine, diethylaniline and pyridine) or an inorganic base, e.g., sodium bicarbonate and sodium carbonate, and a solvent, e.g., a halogenated hydrocarbon (e.g., methylene chloride and chloroform), tetrahydrofuran, acetonitrile, dimethyl formamide, dimethyl acetamide and mixtures thereof and an aqueous mixture thereof.

The acylation may be conducted at a temperature ranging from −50° C. to 50° C., preferably from −30° C. to 20° C., and the acylating agent may be used in a stoichiometric amount, or an excess(1.05 to 1.2 equivalents) thereof, based on the compound of formula(V).

In order to prepare the compound of formula(I), amino or carboxyl protecting groups of formula(II) can be readily removed by any of the conventional deprotecting methods which are well known in the field of cephalosporin antibiotics. For example, acid- or base-hydrolysis or reduction is generally applicable. For example, when the compound of formula(II) comprises an amido group as a protecting group, the compound may be subjected to an aminohalogenation, aminoetherification and hydrolysis procedure. The acid-hydrolysis is suitable for removing a tri(di)phenylmethyl or alkoxycarbonyl group; and may be conducted by employing an organic acid, e.g., formic acid, trifluoroacetic acid and p-toluenesulfonic acid, or an inorganic acid, e.g., hydrochloric acid.

The reaction for introducing the compound(III) into the 3-position of the compound(II) to prepare the compound(I) is carried out in the presence of a solvent or mixtures thereof such as lower alkylnitrile, e.g., acetonitrile and propionitrile, lower halogenated alkane, e.g., chloromethane, dichloromethane and chloroform, ether, e.g., dimethylformamide, ester, e.g., ethylacetate, ketone, e.g., acetone, hydrocarbon, e.g., benzene, a cohol, e.g., methanol and ethanol, and sulfoxide, e.g., dimethylsulfoxide, wherein the temperature may range from −10 to 80° C., more preferably from 20 to 40° C.; and the compounds of the formula(III) are used in an amount of 0.5 to 2 molar equivalents, more preferably 1.0 to 1.1 molar equivalents, based on the compounds of formula(II).

The separation and purification of the compounds(I) can be carried out by using a conventional method such as recrystallization, column chromatography over silica gel or ion-exchange chromatography.

The compounds of formula(I) and non-toxic salts such as salts with alkali metal, alkaline earth metal, inorganic acid, organic acid or amino acid in accordance with the present invention, as described above, exhibit potent and broad antibacterial activities against Gram-positive bacteria and a variety of Gram-negative bacteria as well particularly against
Pseudomonas.

Also, these compounds have high stability to β lactamases produced by a number of Gram-negative bacteria.

The pharmaceutical compositions of the invention may be formulated for administration in unit dose or multi-dose containers. The compositions may take various forms such as solution, suspension or emulsion in an oily or aqueous vehicle, which can contain conventional additives such as a dispersant, suspending agent, stabilizer and the like. Alternatively, the active ingredient may be formulated into a dried powder that can be normally dissolved in an aqueous solution of sterile pyrogen-free water before use. The compositions may be also formulated into suppositories containing conventional suppository bases such as cocoa butter or other glycerides.

The pharmaceutical compositions in a unit dose form may preferably comprise about 50 to 1,500mg of the active ingredient, depending on the age and body weight of the patient, the nature and severity of the illness, and so on. In general, it has been shown advantageous to administer the active compounds in an amount ranging from 500 to 5,000mg per day in order to achieve the desired results, depending on the routes and frequency of administration. In case of intramuscular or intravenous administration for adult human treatment, the dosage of about 150 to 3,000mg per day is thought to be sufficient, although it may vary in case of treatment for specific infections caused by certain strains.

Exemplary compounds of formula(I) of the present invention are as follows:

I-1: 7-[(Z)-2-(aminothiazol-4-yl) -2-(α-carboxy-3,4-dihydroxybenzyloxyimino) acetamido]-3-(4,6-diaminopyrimidine-2-yl) thiomethyl-3-cephem-4-carboxylate

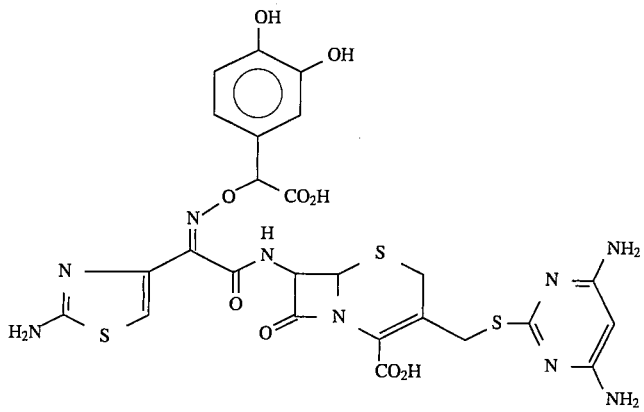

I-2: 7-[(Z)-2-(aminothiazol-4-yl)-2-(α-carboxy-3,4- dihydroxybenzyloxyimino) acetamido]-3-(4,6-diamino -5-methylpyrimidine-2-yl) thiomethyl-3-cephem-4-carboxylate

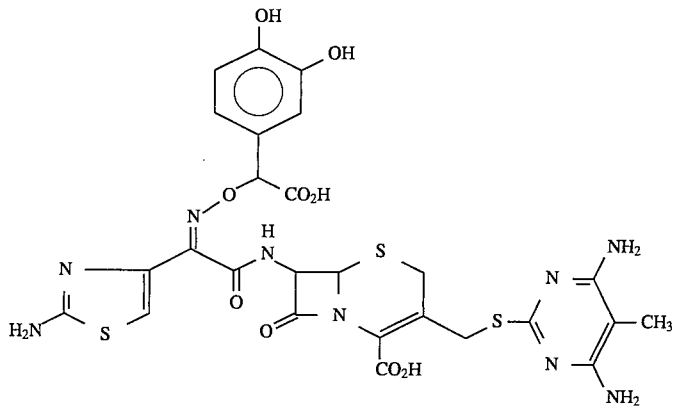

I-3 7-[(Z)-2-(aminothiazol-4-yl)-2-(α-carboxy-3,4-dihydroxybenzyloxyimino) acetamido]-3-(4-aminopyrimidine-2-yl) thiomethyl-3-cephem-4-carboxylate

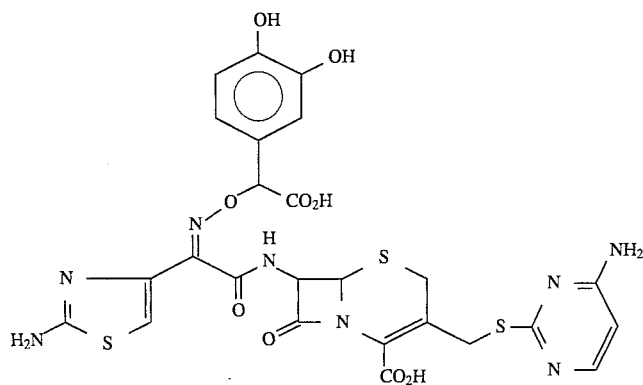

I-4 : 7-[(Z)-2-(aminothiazol-4-yl)-2-(α-carboxy-3,4-dihydroxybenzyloxyimino) acetamido]-3-(4-amino-5,6-cyclopentapyrimidine-2-yl) thiomethyl-3-cephem-4-carboxylate

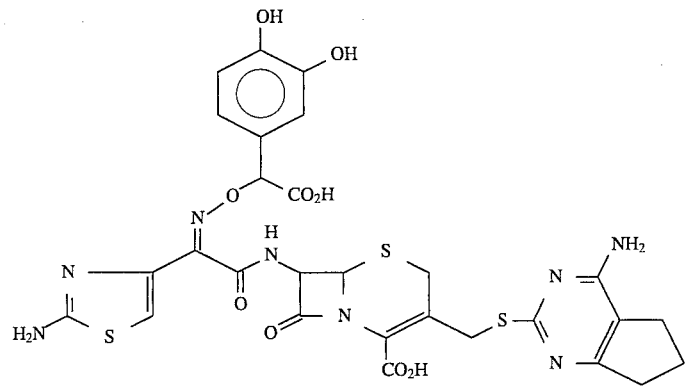

I-5 : 7-[(Z)-2-(aminothiazol-4-yl)-2-(α-carboxy-3,4-dihydroxybenzyloxyimino) acetamido]-3-(4,5,6-triaminopyrimidine-2-yl) thiomethyl-3-cephem-4-carboxylate

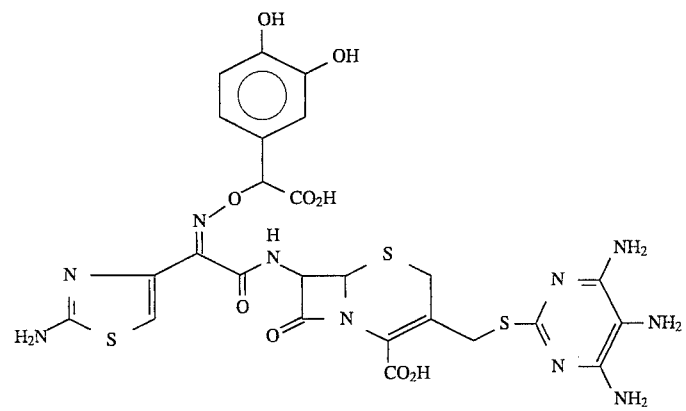

I-6 : 7-[(Z)-2-(aminothiazol-4-yl)-2-(α-carboxy-3,4-dihydroxybenzyloxyimino) acetamido]-3-(2,6-diaminopyrimidine-4-yl) thiomethyl-3-cephem-4-carboxylate

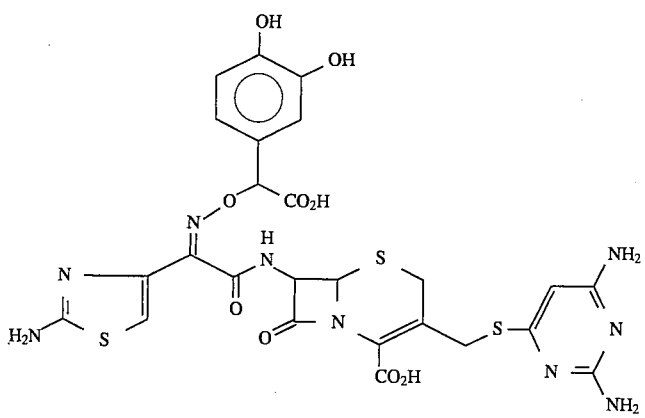

I-7: 7-[(Z)-2-(aminothiazol-4-yl)-2-(α-carboxy-3,4-dihydroxybenzyloxyimino) acetamido]-3-(6-aminopyrimidine-4-yl) thiomethyl-3-cephem-4-carboxylate

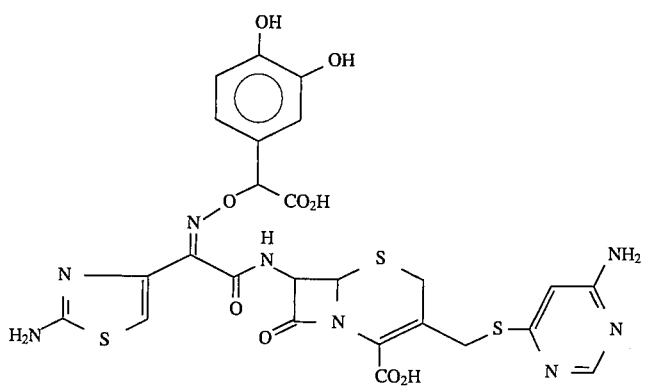

The following Preparation Examples and Examples illustrate how some of the starting materials of formulae(II) and (III) and of the compounds of formula(I) can be prepared.

R- and S- diastereoisomers depending on the stereo configuration of the asymmetric carbon on which 7β-dihydroxybenzyl group is attached were obtained in the Examples and they were determined by μ-Bondapak $C_{18}$ Steel Column, using 25% methanol containing 0.5% acetic acid.

PREPARATION EXAMPLE 1

Synthesis of 2-bromo-2-(3,4-O-isopropylidenedioxyphenyl)acetic acid diphenylmethyl ester Step 1) Synthesis of 2-(3,4-dihydroxyphenyl)-2-hydroxy-1,1,1-trichloroethane 1036g of trichloroacetaldehyde monohydrate was added to a solution of 440g of 1,2-dihydroxybenzene dissolved in 1L of methylenechloride and the resultant solution was cooled to 0° C. 102g of triethylamine was added dropwise to the solution and heated to room temperature. After stirring for about 20 min., the reaction solution was heated to 50° C. and further stirred for 3 hours at that temperature. After the completion of the reaction, the solution was evaporated under reduced pressure to remove methylene chloride and the residue obtained was dissolved in 4L of ethyl acetate. The resultant solution was washed with 2,400ml of 0.5N hydrochloric acid and 2L of saturated sodium chloride solution, subsequently. The resultant was dried on anhydrous magnesium sulfate and distilled under reduced pressure to obtain 540g of the title compound.

NMR(δ, acetone-$d_6$): 5.2(d, 1H), 6.0(d, 1H), 6.8(d, 1H), 7.0(dd, 1H), 7.2(d, 1H), 7.9(s, 1H), 8.0(s, 1H)

Step 2) Synthesis of α-trichloromethyl-3,4-isopropylidenedioxy benzylalcohol 515g of the compound obtained in step 1 was dissolved in 2.5L of benzene and thereto were added 305ml of 2,2-dimethoxypropane and 2.84g of phosphorous pentoxide. The reaction mixture was heated under reflux for 2 hours. The reaction was carried out with a reactor equipped with a soxhlet extractor filled with 600g of calcium chloride to remove by-product methanol. After 2 hours, 77ml of 2,2-dimethoxypropane was added to the mixture, the resultant was further refluxed for 3 hours, cooled to room temperature, washed four times with 500ml of 1N aqueous sodium carbonate solution and 500ml of saturated sodium chloride solution, subsequently, dried on anhydrous magnesium sulfate and distilled under reduced pressure. The residue thus obtained was purified with silicagel column chromatography to obtain 220g of the title compound.

NMR(δ, $CDCl_3$): 1.66(s, 6H), 3.61(d, 1H), 4.98(d, 1H), 6.53-6.90(m, 3H)

Step 3) Synthesis of 2-(3,4-O-isopropylidenedioxyphenyl)-2-hydroxyacetic acid 119.4g of lithium hydroxide monohydrate was dissolved in 500ml of water and the resultant solution was cooled to 0° C. Thereto were added 201g of the compound obtained in step 2 and 413ml of dioxane and the resultant mixture was stirred for 3 days at room temperature. 240g of ice was added thereto, the mixture was stirred for 30 min. with further adding 300ml of 6N hydrochloric acid and 120g of ice. The resultant was filtered, washed with 1.8L of water and then 700ml of chloroform, and dried under nitrogen atomsphere to obtain 60g of the title compound.

NMR($\delta$, DMSO-$d_6$): 1.61(s, 6H) -4.85(s, 1H), 6.60-6.83(m, 3H), 8.2(bs, 2H)

Step 4) Synthesis of 2-(3,4-O-isopropylidenedioxyphenyl)-2-hydroxyacetic acid diphenylmethyl ester 50g of the compound obtained in step 3 was dissolved in 400ml of acetone and thereto was added dropwise 1M diphenyldiazo-methane dissolved in diethylether until nitrogen gas occurred no more. The reaction mixture was further stirred for 20 min., distilled under reduced pressure and purified with silicagel column chromatography to obtain 70g of the title compound.

NMR($\delta$, $CDCl_3$): 1.69(s, 6H), 5.62(d, 1H), 6.20(d, 1H), 6.70(d, 1H), 6.87(s, 1H), 6.89(d, 1H), 6.97(s, 1H), 7.26(b, 10H)

Step 5) Synthesis of 2-bromo-2-(3,4-O-isopropylidenedioxyphenyl)acetic acid diphenylmethyl ester 108g of the compound obtained in step 4 was dissolved in 1.3L of dimethylformamide and the resultant solution was cooled to -60° C. Thereto was added 187.4g of phosphorous tribromide and the resultant solution was warmed to -15° C., stirred for 20 min. and distilled under reduced pressure. The residue thus obtained was dissolved in 1L of ethylacetate and the resultant solution was washed with 1L of saturated sodium chloride solution four times, dried on anhydrous magnesium sulfate and distilled under reduced pressure to obtain 115.96g of the title compound.

NMR($\delta$, $CDCl_3$): 1.66(d, 6H), 5.41(s, 1H), 6.63(d, 1H), 6.84(s, 1H), 6.86(d, 1H), 6.97(s, 1H), 7.25(d, 10H)

PREPARATION EXAMPLE 2

Synthesis of 2-(2-triphenylmethylamino thiazol-4-yl)-2-($\alpha$-diphenylmethyloxycarbonyl-3,4-O-isopropylidenedioxybenzyloxyimino)acetic acid Step 1) Synthesis of 2-(2-triphenylmethylaminothiazol-4-yl)-2- ($\alpha$-diphenylmethyloxycarbonyl-3,4-O-isopropylidenedioxybenzyl-oxyimino) acetic acid allylester 61g of potassium carbonate and 29.4g of potassium iodide were added to a solution of 58.18g of 2-(2-triphenyaminothiazol-4-yl) -2-hydroxyimino acetic acid-allylester dissolved in 140ml of dimethylformamide and the resultant solution was cooled to 0° C. Thereto was added dropwise a solution of 80.16g of the compound obtained in Preparation Example 1 dissolved in 60ml of dimethyl-formamide for 1 hour and further stirred for 20 min. The resulting solution was distilled under reduced pressure to remove the solvent. The residue thus obtained was dissolved in 2L of ethyl acetate. The resulting solution was washed six times with 400ml of saturated sodium chloride solution, dried on anhydrous magnesium sulfate and distilled under reduced pressure to remove the solvent. The residue thus obtained was purified with silicagel column chromatography to obtain 89g of the title compound.

NMR($\delta$, $CDCl_3$): 1.69(s, 6H), 4.81(d, 2H), 5.27 (ABq, 2H), 5.79(s, 1H), 5.80-5.99(m, 1H), 6.53(s, 1H), 6.64(d, 1H), 6.78(d, 1H), 6.87( s, 1H), 7.13-7.36(m, 27H)

Step 2) Synthesis of 2-(2-triphenylmethylaminothiazol4-yl)-2- ($\alpha$-diphenylmethyloxycarbonyl-3,4-O-isopropylidenedioxybenzyloxyimino)acetic acid 14.5g of potassium 2-ethylhexanoate, 3.75g of triphenylphosphine and 0.6g of tetrakis(triphenylphosphine) palladium were added to a solution of 60g of the compound obtained in step 1 dissolved in 500ml of methylene chloride and stirred for 1 hour at room temperature. The reaction mixture was washed three times with 500ml of saturated sodium chloride solution, dried on anhydrous magnesium sulfate, and distilled under reduced pressure to remove the solvent. The residue thus obtained was purified with silicagel column chromatography to obtain 50g of the title compound.

NMR($\delta$, $CDCl_3$): 1.70(s, 6H), 5.68(s, 1H), 6.55(s, 1H), 6.66(d, 1H), 6.80(d, 1H), 6.89(s, 1H), 7.04-7.27(m, 27H)

PREPARATION EXAMPLE 3

Synthesis of para-methoxybenzyl 3-chloromethyl-7-[(Z)-2-($\alpha$-diphenyloxycarbonyl-3,4-O-isopropylidenedioxy-benzyloxyimino)-2-(2-triphenylmethylaminothiazol-4-yl)acetamido]-3-cephem-4-carboxylate 28.1g of pyridine was added to a solution of 36g of paramethoxybenzyl 7-amino-3-chloromethyl-3-cephem-4-carboxylate suspended in 950ml of methylene chloride. The resultant solution was stirred and cooled to −20° C. Thereto was added 50.09g of the compound obtained in Preparation Example 1 and the reaction solution was stirred for 5 min. 13.62g of phosphorous oxychloride was added to the reaction mixture and further stirred for 30 min. The reaction mixture was washed three times with 400ml of saturated sodium chloride solution and dried on anhydrous magnesium sulfate. The resultant thus obtained was distilled under reduced pressure to remove the solvent and purified with silicagel column chromatography to obtain 70g of the title compound of solid-foam.

NMR($\delta CDCl_3$): 1.59(d, 6H), 3.33(ABq, 2H), 3.83(s, 3H), 4.51(ABq, 2H), 4.96(d, 1H), 6.27(s, 2H), 5.87(dd, 1H), 5.95(s, 1H), 6.6–7.45(m, 35H), 8.21(d, 1H)

Example 1

Synthesis of 7-[(Z)-2-(aminothiazol-4-yl)-2-($\alpha$-carboxy -3,4-dihydroxybenzyloxyimino) acetamido]-3-(4,6-diamino-pyrimidine-2-yl) thiomethyl-3-cephem-4-carboxylate(Compounds I-1S and I-1R)

1.84g of 4,6-diaminopyrimidine-2-thiol was added to a solution of 5.0g of the compound obtained in Preparation Example 3 dissolved in 20ml of dimethylformamide and the resultant was stirred for 1 hour at room temperature. 200ml of distilled water and 200ml of ethyl acetate were added thereto and the resultant was shaken and separated to obtain an organic layer. The organic layer was washed with 200ml of saturated sodium chloride solution three times, dried on 50g of anhydrous magnesium sulfate and evaporated under reduced pressure to remove the solvent. The concentrate thus obtained was added dropwise to 300ml of diethyl ether with stirring to obtain precipitates, which was washed with 200ml. of diethyl ether and dried to obtain 4.62g of white powders. The powders were dissolved in 15ml of anisole and the resultant solution was cooled to 0–4° C. 30ml of trifluoroacetic acid was added dropwise thereto and the reaction mixture was stirred for 1 hour at room temperature and cooled to −10–15° C. Thereto was added dropwise 180ml of diethyl ether and the resultant was filtered, washed with 50ml of acetone and 150ml of diethyl ether, subsequently, and dried to obtain 2.25g of an ivory solid. The solid was isolated by μ-Bondapak $C_{18}$ Steel Column 19mm × 30cm using 5% methanol as an eluent to obtain 460mg of I-1S and 457mg of I-1R of the title compounds as white powders.

M.S (FAB. M+1): 690

NMR (δ, $D_2O$, ÷$NaHCO_3$)

I-1S:3.29(ABq, 2H), 4.07(ABq, 2H), 4.96(d, 1H), 5.37(s, 1H), 5.42(s,1H), 5.62(d, 1H), 6.79~7.02(m,4H).

I-1R:3.31(ABq, 2H), 4.11(ABq, 2H), 4.94(d, 1H), 5.38(s, 1H), 5.41(s, 1H), 5.58(d, 1H), 6.80~7.03(m, 4H).

IR(KBr, $cm^{-1}$): 1770(β-lactam), 1660, 1630, 1570

Example 2

Synthesis of
7-[(Z)-2-(aminothiazol-4-yl)-2-(α-carboxyl
-3,4-dihydroxybenzyloxyimino)acetamido]-3-(4,6-
diamino-5-methylpyrimidine-2-yl)thiomethyl-3-
cephem-4-carboxylate (Compounds I-2S and I-2R)

The same procedures as described in Example 1 were repeated except that 1.99g of 4,6-diamino-5-methylpyrimidine- 2-thiol was used as a starting material to obtain 445mg of I-2S and 443mg of I-2R of the title compounds.

M.S (FAB, M+1): 704

NMR (δ, $D_2O$ +$NaHCO_3$)

I -2S: 1.83 (s, 3H ), 3.33 (ABq, 2H), 4.11(ABq, 2H), 4.94(d, 1H), 5.39(s,1H), 5.59(d, 1H), 6.80~7.03(m, 4H).

I-2R:1.84(s,3H), 3.32(ABq, 2H), 4.09(ABq, 2H), 4.95(d, 1H), 5.39(s, 1H), 5.62(d, 1H), 6.80~7.03(m, 4H).

IR (KBr, $cm^{-1}$): 1770(β-lactam), 1665, 1630, 1580

Example 3

Synthesis of
7-[(Z)-2-(aminothiazol-4-yl)-2-(α-carboxyl-3,4-
dihydroxybenzyloxyimino)
acetamido]-3-(4-amino-pyrimidine-2-yl)
thiomethyl-3-cephem-4-carboxylate(Compounds
I-3S and I-3R)

The same procedures as described in Example 1 were repeated except that 1.72g of 4-aminopyrimidine-2-thiol was used as a starting material to obtain 450mg of I-3S and 454mg of I-3R of the title compounds.

M.S (FAB, M+1): 675

NMR (δ, $D_2O$ +$NaHCO_3$)

I-3S:3.30(ABq, 2H), 4.09(ABq, 2H), 4.98(d, 1H), 5.36(s, 1H), 5.62(d, 1H), 6.49(d, 1H), 6.81~7.02(m, 4H), 7.96(d, 1H).

I-3R:3.31(ABq. 2H), 4.11(ABq, 2H), 4.96(d, 1H), 5.38(S, 1H), 5.63(d, 1H), 6.49(d. 1H), 6.82~7.01(m, 4H), 7.98(d, 1H).

IR(KBr, $cm^{-1}$): 1770(β-lactam), 1670, 1630, 1570

Example 4:

Synthesis of
7-[(Z)-2-(aminothiazol-4-yl)-2-(α-carboxyl-3,4-
dihydroxybenzyioxyimino)acetamido]-3-(4-amino-5,6-
cyclopentapyrimidine-2-yl)thiomethyl-3-cephem-4-
carboxylate (Compounds I-4S and I-4R)

The same procedures as described in Example 1 were repeated except that 2.23g of 4-amino-5,6-cyclopentapyrimidine-2-thiol was used as a starting material to obtain 438mg of I-4S and 441mg of I-4R of the title compounds.

M.S (FAB. M+1): 715

NMR (δ, $D_2O$ +$NaHCO_3$)

I-4S: 2.12(m, 2H), 2.68(t,2H), 2.95(t,2H), 3.34(ABq, 2H), 4.23(ABq, 2H), 4.96(d, 1H), 5.38(s, 1H), 5.54(d, 1H), 6.81~7.02(m, 4H).

I -4R: 2.11(m, 2H), 2.69(t,2H), 2.95(t,2H), 3.33(ABq, 2H), 4.22(ABq, 2H) 4.97(d, 1H), 5.38(s, 1H), 5.59(d, 1H), 6.80~7.02(m, 4H).

IR(KBr, $cm^{-1}$): 1770(β-lactam), 1665, 1635, 1580

Example 5

Synthesis of
7-[(Z)-2-(aminothiazol-4-yl)-2-(α-carboxy-3,4-
dihydroxybenzyloxyimino)acetamido]-3-(4,5,6-
triaminopyrimidine-2-yl)thiomethyl-3-cephem-4-
carboxylate (Compounds I-5S and I-5R)

The same procedures as described in Example 1 were repeated except that 2g of 4,5,6-triaminopyrimidine-2-thiol was used as a starting material to obtain 510mg of I-5S and 520mg of I-5R of the title compounds.

M.S (FAB, M+1): 705

NMR (δ, $D_2O$ +$NaHCO_3$)

I-5S: 3.31 (ABq, 2H), 4.07(ABq, 2H), 4.96(d, 1H), 5.40(s, 1H), 5.65(d, 1H), 6.80~7.05(m, 4H).

I-5R: 3.32(ABq, 2H), 4.11(ABq, 2H), 4.95(d, 1H), 5.41(s, 1H), 5.63(d, 1H), 6.80~7.01 (m, 4H).

IR(KBr, $cm^{-1}$): 1770(β-lactam), 1670, 1620, 1580

Example 6

Synthesis of
7-[(Z)-2-(aminothiazol-4-yl)-2-(α-carboxy-3,4-
dihydroxybenzyloxyimino)acetamido]-3-(2,6-diamino-
pyrimidine-4-yl)thiomethyl-3-cephem-4-carboxylate
(Compounds I-6S and I-6R)

The same procedures as described in Example 1 were repeated except that 1.84g of 2,6-diaminopyrimidine-2-thiol was used as a starting material to obtain 510mg of I-6S and 490mg of I-6R of the title compounds.

MS(FAB, M+1): 690

NMR (δ, $D_2O$ +$NaHCO_3$)

I-6S: 3.30(ABq, 2H), 4.05(ABq, 2H), 4.98(d, 1H). 5.41(s, 1H), 5.65(d. 1H), 5.89(S, 1H), 6.79~7.02(m, 4H)

I-6R : 3.31 (ABq. 2H). 4.10(ABq, 2H). 4.97(d. 1H), 5.39(S. 1H). 5.61(d. 1H). 5.89(S. 1H). 6.80~7.03(m, 4H)

IR(KBr, $cm^{-1}$): 1770(β-lactam), 1670, 1630, 1580

Example 7

Synthesis of
7[-(Z)-2-(aminothiazol-4-yl)-2-(α-carboxy-3,4-
dihydroxybenzyloxyimino)acetamido]-3-(6-amino-
pyrimidine-4-yl)thiomethyl-3cephem-4-carboxylate
(Compounds I-7S and I-7R)

The same procedures as described in Example 1 were repeated except that 1.99g of 6-aminopyrimidine-4-thiol. was used as a starting material to obtain 420mg of I-7S and 410mg of I-7R of the title compounds.

MS(FAB. M+1): 675

NMR(δ, $D_2O$ +$NaHCO_3$ )

I-7S: 3.33(ABq, 2H), 4.11(ABq, 2H), 4.94(d, 1H), 5.59(d, 1H). 5.89(s, 1H), 6.80~7.03(m, 4H), 8.19(s, 1H)

I-7R: 3.32(ABq, 2H), 4.09(ABq, 2H), 4.95(d,1H), 5.62(d, 1H), 5.91 (s, 1H), 6.80~7.03(m, 4H), 8.20(s, 1H)

IR(KBr, cm$^{-1}$): 1770($\beta$-lactam), 1650, 1630, 1580

ACTIVITY TEST

In order to illustrate surprisingly superior antibacterial effectiveness of the compounds of the present invention, the minimal inhibitory concentrations(MIC) and the pharmakinetic variables of the compounds synthesized against standard strains were determined and compared with Ceftazidime, which was used as a control compound.

These MIC values were taken by employing a two-fold dilution method: that is, two-fold serial dilutions of each of the test compounds were made and dispersed in a Muller-Hinton agar medium; 2μl of the standard test strain which had the $10^7$ CFU(Colony Forming Unit) per ml was inoculated on the medium; and these were incubated at 37° C. for 20 hours. The results of the MIC tests are shown in Table 1.

The pharmakinetic variables were determined using SD rats (♂) of a body weight of 230±10g as follows. The "S" compound of each of the Examples was injected to femoral vein of 4–5 rats by 20mg/Kg and then blood was collected from femoral artery in 1, 2.5, 5, 10, 20, 40, 60 and 120 min. The pharmakinetic variables were determined from the concentration of the compound in blood by agar well method and the results are shown in Table 2.

TABLE 1

| Strains | Compounds | | | | | | | | | |
|---|---|---|---|---|---|---|---|---|---|---|
| | I-1S | I-1R | I-2S | I-2R | I-3S | I-3R | I-4S | I-4R | I-5S | I-5R |
| *Staphylococcus aureus* 6538P | 2 | 2 | 1 | 2 | 2 | 2 | 1 | 2 | 2 | 2 |
| *Staphylococcus aureus* giorgio | 1 | 1 | 1 | 1 | 1 | 2 | 1 | 2 | 1 | 1 |
| *Staphylococcus aureus* 77 | 8 | 32 | 4 | 32 | 4 | 16 | 8 | 32 | 8 | 32 |
| *Staphylococcus aureus* 241 | 64 | 128 | 64 | 128 | 128 | 128 | 64 | 128 | 64 | 128 |
| *Staphylococcus epidermidis* 887E | 32 | 64 | 16 | 64 | 32 | 64 | 32 | 32 | 32 | 64 |
| *Streptococcus laecalis* 29212A | 4 | 16 | 4 | 32 | 4 | 32 | 4 | 16 | 4 | 16 |
| *E. coli* 10536 | ≦0.008 | 0.063 | ≦0.008 | 0.063 | ≦0.008 | 0.031 | ≦0.008 | 0.063 | ≦0.008 | 0.063 |
| *E. coli* 3190Y | 0.031 | 0.13 | 0.063 | 0.13 | 0.031 | 0.13 | 0.031 | 0.25 | 0.031 | 0.063 |
| *E. coli* 851E | 0.031 | 0.13 | 0.031 | 0.13 | 0.063 | 0.13 | 0.031 | 0.13 | 0.031 | 0.13 |
| *E. coli* TEM1 1193E | 0.031 | 0.25 | 0.031 | 0.5 | 0.031 | 0.5 | 0.063 | 0.5 | 0.031 | 0.25 |
| *E. coli* TEM3 3455E | 0.016 | 0.25 | 0.016 | 0.25 | 0.016 | 0.25 | 0.016 | 0.25 | 0.016 | 0.25 |
| *E. coli* TEM5 3739E | 0.063 | 0.25 | 0.063 | 0.25 | 0.063 | 0.25 | 0.063 | 0.25 | 0.063 | 0.25 |
| *E. coli* TEM7 3457E | ≦0.008 | 0.063 | ≦0.008 | 0.016 | 0.063 | 0.016 | ≦0.008 | 0.063 | ≦0.008 | 0.063 |
| *E. coli* TEM9 2639E | 0.25 | 0.5 | 0.25 | 0.5 | 0.25 | 0.5 | 0.25 | 0.5 | 0.25 | 0.5 |
| *Pseudomonas aeruginosa* 1912E | 0.25 | 1 | 0.5 | 2 | 0.25 | 1 | 0.25 | 2 | 0.25 | 1 |
| *Pseudomonas aeruginosa* 10145 | 0.13 | 2 | 0.13 | 2 | 0.13 | 2 | 0.13 | 2 | 0.13 | 2 |
| *Pseudomonas aeruginosa* 6065 | 0.25 | 8 | 0.25 | 8 | 0.5 | 8 | 0.13 | 8 | 0.25 | 8 |
| *Acinetobacter* 15473A calcoaceticus | 0.13 | 1 | 0.25 | 1 | 0.13 | 1 | 0.13 | 1 | 0.13 | 1 |
| *Citrobacter diversus* 2046E | 0.063 | 1 | 0.016 | 2 | 0.031 | 2 | 0.063 | 2 | 0.063 | 1 |
| *Enterobacter* IND + VE 1194E cloacae | 2 | 32 | 4 | 32 | 2 | 32 | 2 | 32 | 2 | 32 |
| *Enterobacter* P99 cloacae | 16 | 32 | 8 | 32 | 8 | 16 | 8 | 32 | 8 | 32 |
| *Klebsiella* SHV-1 1976E aerogenes | 0.13 | 0.5 | 0.13 | 0.5 | 0.13 | 1 | 0.13 | 0.5 | 0.13 | 0.25 |
| *Klebsiella* K1 + 1082E aerogenes | 0.031 | 0.5 | 0.031 | 1 | 0.031 | 0.5 | 0.031 | 1 | 0.031 | 0.5 |
| *Proteus vularis* 6059A | 0.13 | 0.5 | 0.13 | 0.5 | 0.13 | 0.5 | 0.13 | 0.5 | 0.13 | 0.5 |
| *Serratia marcescens* 1826E | 0.25 | 2 | 0.25 | 2 | 0.25 | 2 | 0.25 | 2 | 0.25 | 2 |
| *Salmonella typhimurium* 14028A | 0.016 | 0.13 | 0.016 | 0.25 | 0.016 | 0.013 | 0.016 | 0.13 | 0.016 | 0.13 |

| Strains | Compounds | | | | |
|---|---|---|---|---|---|
| | I-6S | I-6R | I-7S | I-7R | Ceftazidime |
| *Staphylococcus aureus* 6538P | 1 | 1 | 2 | 2 | 16 |
| *Staphylococcus aureus* giorgio | 1 | 1 | 1 | 2 | 4 |
| *Staphylococcus aureus* 77 | 8 | 16 | 4 | 8 | 32 |
| *Staphylococcus aureus* 241 | 64 | 64 | 64 | 128 | >128 |
| *Staphylococcus epidermidis* 887E | 32 | 32 | 32 | 32 | >128 |
| *Streptococcus laecalis* 29212A | 2 | 4 | 2 | 4 | >128 |
| *E. coli* 10536 | ≦0.008 | 0.016 | ≦0.008 | 0.016 | 0.13 |
| *E. coli* 3190Y | 0.031 | 0.063 | 0.031 | 0.063 | 0.063 |
| *E. coli* 851E | 0.031 | 0.063 | 0.063 | 0.13 | 0.063 |
| *E. coli* TEM1 1193E | 0.031 | 0.063 | 0.063 | 0.13 | 0.25 |
| *E. coli* TEM3 3455E | 0.016 | 0.031 | 0.016 | 0.031 | 8 |
| *E. coli* TEM5 3739E | 0.063 | 0.063 | 0.063 | 0.063 | 8 |
| *E. coli* TEM7 3457E | ≦0.008 | 0.016 | 0.016 | 0.031 | 16 |
| *E. coli* TEM9 2639E | 0.13 | 0.25 | 0.13 | 0.25 | >128 |
| *Pseudomonas aeruginosa* 1912E | 0.13 | 0.25 | 0.25 | 0.25 | 1 |
| *Pseudomonas aeruginosa* 10145 | 0.25 | 0.25 | 0.25 | 2 | 2 |
| *Pseudomonas aeruginosa* 6065 | 0.25 | 1 | 0.5 | 4 | 16 |

TABLE 1-continued

|  | | | | | |
|---|---|---|---|---|---|
| *Acinetobacter* 5473A *calcoaceticus* | 0.13 | 0.25 | 0.13 | 0.25 | 2 |
| *Citrobacter diversus* 2046E | 0.063 | 0.13 | 0.063 | 0.13 | 0.5 |
| *Enterobacter* IND + VE 1194E *cloacae* | 2 | 4 | 2 | 4 | 128 |
| *Enterobacter* P99 *cloacae* | 8 | 8 | 8 | 8 | 64 |
| *Klebsiella* SHV-1 1976E *aerogenes* | 0.13 | 0.25 | 0.25 | 0.25 | 0.25 |
| *Klebsiella* K1 + 1082 E *aerogenes* | 0.031 | 0.25 | 0.063 | 0.25 | 0.25 |
| *Proteus vularis* 6059A | 0.13 | 0.25 | 0.25 | 0.25 | 0.063 |
| *Serratia marcescens* 1826E | 0.13 | 0.5 | 0.25 | 0.5 | 0.25 |
| *Salmonella typhimurium* 14028A | 0.016 | 0.13 | 0.016 | 0.13 | 0.25 |

TABLE 2

| | Compounds | | | | | | | |
|---|---|---|---|---|---|---|---|---|
| Variables | I-1S | I-2S | I-3S | I-4S | I-5S | I-6S | I-7S | Ceftazidime |
| $T_{1/2}$ (min) | 62 | 55 | 58 | 57 | 59 | 62 | 59 | 20 |
| AUC(μg. min/ml) | 3694 | 3247 | 3472 | 3329 | 3571 | 3589 | 3601 | 1863 |

What is claimed is:

1. A cephalosporin compound of formula (I):

(I)

wherein:

$R^1$ is a hydrogen or an amino protecting group;

$R^2$ and $R^3$ are, independently, a hydrogen or a hydroxy protecting group, or form together a cyclic diol protecting group;

$R^4$ and $R^5$ are, independently, a hydrogen or a carboxyl protecting group;

X and Y are a nitrogen and a carbon atom, respectively, or a carbon and a nitrogen atom, respectively;

$R^6$ and $R^7$ are, independently, a hydrogen or an amino, hydroxy, alkoxy, $C_{1-4}$ alkyl, carboxyl or alkoxy carbonyl group, or jointly form a $C_{3-7}$ cycloalkyl group together with the carbon to which they are attached, when X and Y are a nitrogen and a carbon, respectively, or $R^7$ is a hydrogen or an amino group when X and Y are a carbon and a nitrogen, respectively; and Q is =CH— or =N—, or pharmacologically acceptable non-toxic salts, physiologically hydrolyzable esters, and solvates and isomers thereof.

2. The compound of claim 1 wherein all of $R^1$ $R^4$ and $R^5$ are a hydrogen; $R^2$ and $R^3$ are independently a hydrogen or an acetyl group; $R^6$ is a hydrogen or a methyl group and $R^7$ is a hydrogen or an amino group, or they form a cyclopentane or cyclohexane ring; and X and Y are a nitrogen and a carbon atom, respectively.

3. The compound of claim 1 wherein all of $R^1$, $R^4$ and $R^5$ are a hydrogen; $R^2$ and $R^3$ are independently a hydrogen or an acetyl group; $R^7$ is a hydrogen or an amino group; and X-and Y are a carbon and a nitrogen atom, respectively.

4. The compound of claim 1 wherein the compound is selected from the group consisting of:

7-[(Z)-2-(aminothiazol-4-yl)-2-((R)-α-carboxy-3,4-dihydroxybenzyloxyimino)acetamido]-3-(4,6-diaminopyrimidine-2-yl)thiomethyl-3- cephem-4-carboxylate;

7-[(Z)-2-(aminothiazol-4-yl)-2-((S)-α-carboxy-3,4-dihydroxybenzyl- oxyimino)acetamid]-3-(4,6-diaminopyrimidine-2-yl)thiomethyl-3-cephem-4-carboxylate;

7-[(Z)-2-(aminothiazol-4-yl)-2-((R)-α-carboxy-3,4-dihydroxybenzyloxyimino)acetamido]-3-(4,6-diamino-5-methylpyrimidine-2-yl) thiomethyl-3-cephem-4-carboxylate;

7-[(Z)-2-(aminothiazol-4-yl)-2-((S)-α-carboxy-3,4-dihydroxybenzyloxyimino)acetamido]-3-(4,6-diamino-5-methylpyrimidine-2-yl) thiomethyl-3-cephem-4-carboxylate;

7-[(Z)-2-(aminothiazol-4-yl)-2-((R)-α-carboxy-3,4-dihydroxybenzyloxyimino)acetamido]-3-(4-aminopyrimidine-2-yl)thiomethyl-3-cephem4-carboxylate;

7-[(Z)-2-(aminothiazol-4-yl)-2-((S)-α-carboxy-3,4-dihydroxybenzyloxyimino)acetamido]-3-(4-aminopyrimidine-2-yl)thiomethyl-3-cephem4-carboxylate;

7-[(Z)-2-(aminothiazol-4-yl)-2-((R)-α-carboxy-3,4-dihydroxybenzyloxyimino)acetamido]-3-(4-amino-5,6-cyclopentapyrimidine-2-yl) thiomethyl-3-cephem-4-carboxylate;

7-[(Z)-2-(aminothiazol-4-yl)-2-((S)-α-carboxy-3,4-dihydroxybenzyloxyimino)acetamido]-3-(4-amino-5,6-cyclopentapyrimidine-2-yl) thiomethyl-3-cephem-4-carboxylate;

7-[(Z)-2-(aminothiazol-4-yl)-2-((R)-α-carboxy-3,4-dihydroxybenzyloxyimino)acetamido]-3-(4,5,6-triaminopyrimidine-2-yl)thiomethyl-3- cephem-4-carboxylate;

7-[(Z)-2-(aminothiazol-4-yl)-2-((S)-α-carboxy-3,4-dihydroxybenzyloxyimino)acetamido]-3-(4,5,6-triaminopyrimidine-2-yl)thiomethyl-3- cephem-4-carboxylate;

7-[(Z)-2-(aminothiazol-4-yl)-2-((R)-α-carboxy-3,4-dihydroxybenzyloxyimino)acetamido]-3-(2,6-diaminopyrimidine-4-yl)thiomethyl-3-cephem-4-carboxylate;

7-[(Z)-2-(aminothiazol-4-yl)-2-((S)-α-carboxy-3,4-dihydroxybenzyloxyimino)acetamido]-3-(2,6-diaminopyrimidine-4-yl)thiomethyl-3-cephem-4-carboxylate;

7-[(Z)-2-(aminothiazol-4-yl)-2-((R)-α-carboxy-3,4-dihydroxybenzyloxyimino)acetamido]-3-(6-aminopyrimidine-4-yl)thiomethyl-3-cephem4-carboxylate; 7-[(Z)-2-(aminothiazol-4-yl)-2-((S)-α-carboxy-3,4-dihydroxybenzyloxyimino)acetamido]-3-(6-aminopyrimidine-4-yl)thiomethyl-3-cephem-4-carboxylate; and mixtures thereof.

5. A pharmaceutical composition comprising a therapeutically effect of a cepharosporin compound according to claim 1 and a pharmaceutically acceptable carrier thereof.

* * * * *